United States Patent
Belowich et al.

(10) Patent No.: US 11,760,713 B2
(45) Date of Patent: Sep. 19, 2023

(54) BENZOPHENONE DERIVATIVE

(71) Applicants: Dow Global Technologies LLC, Midland, MI (US); Rohm and Haas Company, Collegeville, PA (US)

(72) Inventors: Matthew E. Belowich, Midland, MI (US); Alvin M. Maurice, Lansdale, PA (US); Jordan Stracke, Midland, MI (US); Mark D. Westmeyer, Collegeville, PA (US)

(73) Assignees: Dow Global Technologies LLC, Midland, MD (US); Rohm and Haas Company, Collegeville, PA (US)

( * ) Notice: Subject to any disclaimer, the term of this patent is extended or adjusted under 35 U.S.C. 154(b) by 341 days.

(21) Appl. No.: 17/297,517

(22) PCT Filed: Dec. 2, 2019

(86) PCT No.: PCT/US2019/063912
§ 371 (c)(1),
(2) Date: May 27, 2021

(87) PCT Pub. No.: WO2020/131338
PCT Pub. Date: Jun. 25, 2020

(65) Prior Publication Data
US 2022/0017445 A1     Jan. 20, 2022

Related U.S. Application Data

(60) Provisional application No. 62/780,496, filed on Dec. 17, 2018.

(51) Int. Cl.
| | | |
|---|---|---|
| C07C 49/84 | (2006.01) |
| C08F 220/14 | (2006.01) |
| C09D 133/14 | (2006.01) |
| C09D 4/00 | (2006.01) |
| C08F 2/50 | (2006.01) |

(52) U.S. Cl.
CPC ............ *C07C 49/84* (2013.01); *C08F 220/14* (2013.01); *C09D 4/00* (2013.01); *C09D 133/14* (2013.01); *C08F 2/50* (2013.01)

(58) Field of Classification Search
CPC .......... C07C 49/84; C08F 220/14; C09D 4/00
See application file for complete search history.

(56) References Cited

U.S. PATENT DOCUMENTS

| | | | |
|---|---|---|---|
| 4,602,097 A | 7/1986 | Curtis | |
| 5,314,936 A | 5/1994 | Schwartz et al. | |
| 2012/0035292 A1* | 2/2012 | Onclin | G03F 7/0048 |
| | | | 252/182.13 |
| 2018/0016376 A1* | 1/2018 | Belowich | C08F 265/06 |
| 2018/0134645 A1* | 5/2018 | Ossenbach | C09D 11/38 |

FOREIGN PATENT DOCUMENTS

| | | |
|---|---|---|
| DE | 102006047863 | 4/2007 |
| EP | 3269784 | 1/2018 |
| WO | 2010081749 | 7/2010 |
| WO | 2011103878 | 9/2011 |
| WO | 2016162389 | 10/2016 |

\* cited by examiner

*Primary Examiner* — Yate' K Cutliff
(74) *Attorney, Agent, or Firm* — Reid S. Willis

(57) ABSTRACT

The present invention relates to a compound which is a benzophenone substituted with a hydroxyl-terminated alkylene oxide group (R) of formula 1:

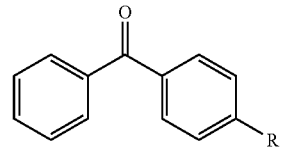

where R is a combination of from 1 to 13 propylene oxide groups and from 5 to 20 ethylene oxide groups, with the proviso that the sum of the propylene oxide groups and the ethylene oxide groups is not greater than 25. The compound of the present invention provides a non-volatile, non-toxic photoinitiator that provides excellent gloss retention in exterior architectural coatings.

6 Claims, No Drawings

BENZOPHENONE DERIVATIVE

BACKGROUND OF THE INVENTION

The present invention relates to a benzophenone derivative, more particularly a benzophenone functionalized with pendant propylene oxide and ethylene oxide repeat units.

Photoinitiators are used in exterior architectural coatings to improve dirt pickup resistance (DPUR) and gloss retention. Norrish type II photoinitiators are especially effective at improving these characteristics, presumably by crosslinking the surface of the polymer film. When excited by UV irradiation, the photoinitiator abstracts a hydrogen from the polymer, creating a reactive radical capable of crosslinking. It is also possible that the photoinitiator generates singlet oxygen via energy transfer to triplet oxygen. This singlet oxygen then reacts to form hydroperoxyl and hydroxyl radicals capable of inducing crosslinking via hydrogen abstraction from the polymer backbone.

Ideally, photoinitiators will improve targeted exterior performance without adversely impacting film flexibility and will have minimal impact on coating color either from the inherent absorption of the photoinitiator or its reaction byproducts. Benzophenone is an example of a photoinitiator that is especially effective for improving coating performance because it is capable of diffusing through the film to the surface before initiating the photo-induced crosslinking reaction. Crosslinking occurs primarily at the film surface because pigments in the coating absorb and/or screen UV light so the photoinitiator is primarily excited near the surface of the film.

Unfortunately, benzophenone has been determined to be a possible human carcinogen (IARC type 2B); moreover, benzophenone is considered a volatile organic compound (VOC) and is undesirable for its adverse environmental impact. This volatility has the additional disadvantage of causing variability in the crosslinking density of the film because benzophenone can evaporate from the film before reacting at the surface. The gloss retention performance of benzophenone is also known to rapidly decline after several months of exposure. Accordingly, it would be highly desirable to find a non-toxic and non-volatile photoinitiator that gives long lasting gloss retention in an exterior architectural coating.

SUMMARY OF THE INVENTION

The present invention addresses a need in the art by providing a compound which is a benzophenone substituted with a hydroxyl-terminated alkylene oxide group (R) of formula 1:

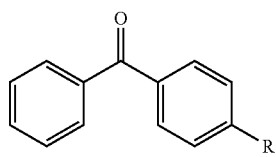

where R is a combination of from 1 to 13 propylene oxide groups and from 5 to 20 ethylene oxide groups, with the proviso that the sum of the propylene oxide groups and the ethylene oxide groups is not greater than 25.

The compound of the present invention provides a non-volatile, non-toxic photoinitiator that provides excellent gloss retention in exterior architectural coatings.

DETAILED DESCRIPTION OF THE INVENTION

The present invention is a compound which is a benzophenone substituted with a hydroxyl-terminated alkylene oxide group (R) of formula 1:

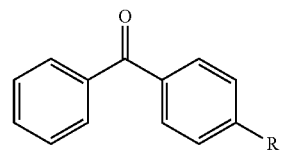

where R is a combination of from 1 to 13 propylene oxide groups and from 5 to 20 ethylene oxide groups, with the proviso that the sum of the propylene oxide groups and the ethylene oxide groups is not greater than 25.

Propylene oxide and ethylene oxide groups are illustrated as follows:

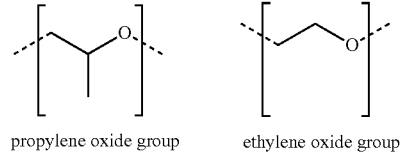

propylene oxide group      ethylene oxide group where the dotted line to the oxygen atom represents a point of attachment to a carbon atom or a terminal hydrogen atom, and the dotted line to the carbon atom represents a point of attachment to an oxygen atom. While it is possible for the groups to be attached in any order, it is preferred that the propylene oxide groups be attached closest to the benzophenone group and that the ethylene oxide groups be attached to the propylene oxide groups, as illustrated in formula 2:

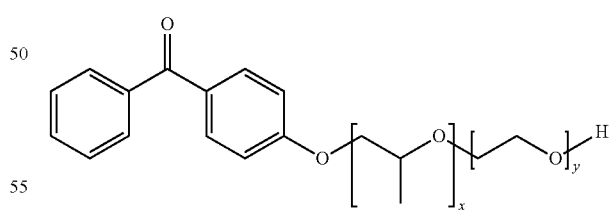

Preferably, x is from 2 to 10, more preferably to 8; and y is preferably from 6, more preferably from 10 to 18, more preferably to 16. Preferably, the number of ethylene oxide groups is greater than the number of propylene oxide groups; that is, preferably, y is greater x. The calculated Log P (cLog P) of the hydroxyl-terminated alkylene oxide group (R), as determined using ChemBioDraw Ultra 13.0 (PerkinElmer), which uses a chemical fragment algorithm method for assessing the partition coefficient of a molecule based on its constituent parts, is preferably in the range of from −4.0, more preferably from −3.5, and most preferably from −3.0, to −1.2, more preferably to −1.3, and most preferably to −1.5.

The functionalized benzophenone is advantageously prepared by base-catalyzed addition of propylene oxide and ethylene oxide to 4-hydroxybenzophenone, in any order or simultaneously. Preferably, the functionalized benzophenone of the present invention is prepared in two steps as follows. In a first step, 4-hydroxybenzophenone and a salt thereof are contacted with propylene oxide and a suitable solvent in a pressure rated reactor; the reactor is heated to a temperature preferably in the range of from 100° C., more preferably from 120° C., to preferably 200° C., more preferably to 150° C. and the propylene oxide is added continuously, then held for a sufficient time to form a poly(propylene oxide)-benzophenone intermediate; ethylene oxide is continuously added to the heated reactor, then held for a sufficient time to afford the desired product. The holding time for both the propylene oxide and ethylene oxide is preferably from 2 to 10 h. The reactor is then cooled and the solvent, which is preferably a high boiling polar aprotic solvent such as dimethoxyethane, is removed to give the alkoxylated benzophenone. The final product is generally a mixture of products having a polydispersity ($M_w/M_n$) preferably in the range of from 1.2 to 3, more preferably to 2.

The alkoxylated benzophenone of the present invention is useful as a photoinitiator in coatings formulations. Accordingly, in another aspect, the present invention is a coating composition comprising an aqueous dispersion of a binder, a rheology modifier, an opacifying pigment, and the alkoxylated benzophenone. The concentration of the alkoxylated benzophenone in the coatings formulation is preferably in the range of from 0.04, more preferably from 0.1 weight percent, to preferably 4, more preferably to 2, and most preferably to 1 weight percent, based on the weight of the coating composition.

The coating composition preferably further includes one or more additives selected from the group consisting of surfactants, dispersants, biocides, defoamers, coalescents, extenders, and colorants.

EXAMPLES

General Alkoxylation Procedure: A 9:1 mol:mol mixture of 4-hydroxybenzophenone and potassium 4-benzoylphenolate in dimethoxyethane (DME) was placed in a pressure-rated reactor having a capacity of 300 mL. The reactor was flushed with nitrogen and heated to 130° C. Propylene oxide (PO) was added continuously over a period of 30 min and then held at this temperature for 6 h. Ethylene oxide (EO) was then added to the reactor over a period of 30 min and held at this temperature for 6 h. The reactor was cooled to room temperature and vented. The solution was removed from the reactor and the solvent was removed in vacuo.

Example 1—Preparation of Benzophenone Derivative: x=5; y=11

Following the general alkoxylation procedure, the benzophenone derivative of FIG. 2, where x is 5 and y is 11, was prepared by addition of PO (10.7 mL, 153 mmol) and EO (19.1 mL, 383 mmol) to a solution of 4-hydroxybenzophenone (3.80 g, 19.2 mmol) and potassium 4-benzoylphenolate (0.45 g, 1.92 mmol) in DME (20 mL). After removal of the solvent in vacuo, 23.1 g (71%) of an oil was isolated.

Example 2—Preparation of Benzophenone Derivative: x=3; y=12

Following the general alkoxylation procedure, the benzophenone derivative of FIG. 2, where x is 3 and y is 12, was prepared by addition of PO (9.7 mL, 139 mmol) and EO (34.8 mL, 696 mmol) to a solution of 4-hydroxybenzophenone (6.90 g, 34.8 mmol) and potassium 4-benzoylphenolate (0.82 g, 3.48 mmol) in DME (35 mL). After removal of the solvent in vacuo, 42.8 g (85%) of an oil was isolated.

Example 3—Preparation of Benzophenone Derivative: x=6; y=6

Following the general alkoxylation procedure, the benzophenone derivative of FIG. 2, where x is 6 and y is 6, was prepared by addition of PO (23.7 mL, 339 mmol) and EO (21.2 mL, 424 mmol) to a solution of 4-hydroxybenzophenone (8.40 g, 42.4 mmol) and potassium 4-benzoylphenolate (1.00 g, 4.24 mmol) in DME (40 mL). After removal of the solvent in vacuo, 40.9 g (79%) of an oil was isolated.

Example 4—Preparation of Benzophenone Derivative: x=3; y=6

Following the general alkoxylation procedure, the benzophenone derivative of FIG. 2, where x is 3 and y is 6, was prepared by addition of PO (14.8 g, 212 mmol) and EO (26.5 mL, 530 mmol) to a solution of 4-hydroxybenzophenone (10.5 g, 53.0 mmol) and potassium 4-benzoylphenolate (1.25 g, 5.30 mmol) in DME (50 mL). After removal of the solvent in vacuo, 41.7 g (82%) of an oil was isolated.

Experimental surfactants were formulated into paints using the formulations in Table 1. Ingredients were added sequentially with continuous stirring using an overhead mixer. ECOSURF™ SA-9 is a non-reactive surfactant (Surfactant in Table 1) that was added to the comparative examples to keep the surfactant level constant. C1 and C2 refer to comparative Examples 1 and 2 respectively. C1 is the paint formulation without any photoinitiator and C2 is the formulation with benzophenone.

Defoamer refers to DOWSIL™ 8590 Defoamer; Microbicide refers to ROCIMA™ 63 Microbicide; Acrylic Binder refers to single stage polymer with the composition: 22 butyl acrylate/27 2-ethylhexyl acrylate/47.25 methyl methacrylate/2.5 methacrylic acid/1.25 ureido methacrylate, with a z-average particle size of 107 nm, a weight percent solids of 46.1% for the inventive examples and C1 (without benzophenone), and 45.3% for C2. BzP refers to benzophenone; Optifilm 400 refers to Optifilm Enhancer 400 Coalescent; RM-3000 refers to ACRYSOL™ RM-3000 Thickener; RM-8W refers to ACRYSOL™ RM-8W Thickener. BzP Ex1-BzP Ex4 refer to the benzophenone derivatives of Examples 1-4. DOWSIL, ROCIMA, ACRYSOL, and ECOSURF are all trademarks of The Dow Chemical Company or Its Affiliates.

TABLE 1

Paint Formulations

| | Paint Example # | | | | | |
|---|---|---|---|---|---|---|
| Material | 1 (g) | 2 (g) | 3 (g) | 4 (g) | C1 (g) | C2 (g) |
| Water | 8.11 | 8.11 | 8.11 | 8.11 | 8.11 | 7.02 |
| Defoamer | 0.10 | 0.10 | 0.10 | 0.10 | 0.10 | 0.10 |

TABLE 1-continued

Paint Formulations

| Material | Paint Example # | | | | | |
|---|---|---|---|---|---|---|
| | 1 (g) | 2 (g) | 3 (g) | 4 (g) | C1 (g) | C2 (g) |
| Ti-Pure R-746 TiO$_2$ | 25.83 | 25.83 | 25.83 | 25.83 | 25.83 | 25.83 |
| Microbicide | 1.10 | 1.10 | 1.10 | 1.10 | 1.10 | 1.10 |
| Acrylic Binder | 64.26 | 64.26 | 64.26 | 64.26 | 64.26 | |
| Acrylic Binder w/BzP | | | | | | 65.36 |
| Optifilm 400 | 0.89 | 0.89 | 0.89 | 0.89 | 0.89 | 0.89 |
| RM-3000 | 1.05 | 1.05 | 1.05 | 1.05 | 1.05 | 1.05 |
| RM-8W | 0.35 | 0.35 | 0.35 | 0.35 | 0.35 | 0.35 |
| BzP Ex1 | 0.30 | | | | | |
| BzP Ex2 | | 0.30 | | | | |
| BzP Ex3 | | | 0.30 | | | |
| BzP Ex4 | | | | 0.30 | | |
| Surfactant | | | | | 0.30 | 0.30 |
| Total | 101.99 | 101.99 | 101.99 | 101.99 | 101.99 | 102.00 |

Gloss Retention Testing

Accelerated weathering was conducted using a QUV instrument (Q-Lab) according to ASTM-D 4587, Standard Practice for Fluorescent UV-Condensation Exposures of Paint and Related Coatings. Paint formulations were drawn down over chromate-treated aluminum panels with a 10 mil applicator and were dried in a controlled environment room (25° C., 50% RH) overnight. Panels were then placed outside (Collegeville, PA) facing South at a 45° angle for 6 d. After outdoor exposure, initial gloss measurements were made. The samples were placed into the QUV and exposed to a cycle consisting of 8 h of UV exposure (0.89 W/m$^2$, UVA lamp) at 60° C. followed by 4 h of a dark condensation period at 50° C. At the end of the 2000-h exposure, the final gloss measurements were made on the samples. Gloss was measured using a BYK Gardner micro-TRI-gloss meter. Table 2 illustrates the Δ60° Gloss after 2006 h of exposure.

TABLE 2

Δ60° Gloss After 2006 h Exposure

| Paint # | Δ60° Gloss |
|---|---|
| 1 | −18.7 |
| 2 | −26.7 |
| 3 | −38.9 |
| 4 | −31.1 |
| C1 | −50.7 |
| C2 | −47.5 |

The data show that the paint formulations containing the benzophenone derivative of the present invention exhibit a markedly lower drift in Δ60° gloss as compared with the formulations that contain benzophenone or no photoinitiator. Though not bound by theory, it is believed that the improved gloss retention observed for the benzophenone derivatives over benzophenone may derive from differences in distribution and stability within the film Benzophenone, being relatively volatile, will more readily migrate through the film and either react or evaporate prematurely from the paint surface, leading to superficial crosslinking of the paint film. In contrast, the inventive benzophenone derivatives are not volatile and therefore cannot evaporate from the film. As the paint surface wears away, the availability of additional photoinitiator for polymer crosslinking leads to improved gloss retention.

It is further believed that the effectiveness of the invention is derived from the surface active nature of the compounds: the combination of hydrophobe (benzophenone) and hydrophile (PO-EO oligomer) will cause the compound to migrate to the latex/water or water/air interfaces; after drying, the photoinitiator may be preferentially located at the film surface. The cLog P of the hydrophile appears to be important; by varying the PO (less hydrophilic) and EO (more hydrophilic) groups of the derivatives, the water sensitivity and gloss retention performance of the paint formulation can be tuned.

The invention claimed is:

1. A compound which is a benzophenone substituted with a hydroxyl-terminated alkylene oxide group (R) of formula 1:

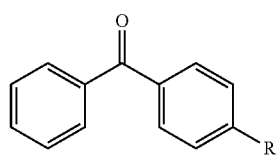

where R is a combination of from 1 to 13 propylene oxide groups and from 5 to 20 ethylene oxide groups, with the proviso that the sum of the propylene oxide groups and the ethylene oxide groups is not greater than 25.

2. The compound of claim 1 wherein the benzophenone substituted with the hydroxyl-terminated alkylene oxide group (R) is represented by formula 2:

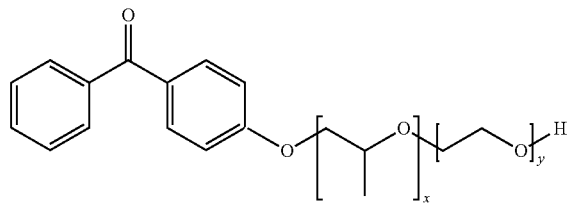

where x is from 2 to 10; and y is from 6 to 18.

3. The compound of claim 2 wherein x is from 2 to 8; and y is from 10 to 16; wherein y is greater x.

4. The compound of claim 2 wherein the calculated Log P of R, as determined using ChemBioDraw Ultra 13.0, is in the range of from −4.0 to −1.2.

5. The compound of claim 4 wherein the calculated Log P of R, as determined using ChemBioDraw Ultra 13.0, is in the range of from −3.5 to −1.3.

6. A coating composition comprising an aqueous dispersion of a binder, a rheology modifier, an opacifying pigment, and from 0.04 to 2 weight percent, based on the weight of the coating composition of the compound of claim 1.

* * * * *